(12) United States Patent
Hiraoka

(10) Patent No.: US 9,511,022 B2
(45) Date of Patent: Dec. 6, 2016

(54) SUSPENSION AND CAKE COMPOSITION CONTAINING CARBOSTYRYL DERIVATIVE AND SILICONE OIL AND/OR SILICONE OIL DERIVATIVE

(75) Inventor: Shogo Hiraoka, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/642,046

(22) PCT Filed: Aug. 19, 2011

(86) PCT No.: PCT/JP2011/069243
§ 371 (c)(1),
(2), (4) Date: Nov. 5, 2012

(87) PCT Pub. No.: WO2012/026562
PCT Pub. Date: Mar. 1, 2012

(65) Prior Publication Data
US 2013/0045250 A1 Feb. 21, 2013

(30) Foreign Application Priority Data

Aug. 24, 2010 (JP) ................. 2010-187107

(51) Int. Cl.
| | | |
|---|---|---|
| *A61K 9/10* | (2006.01) | |
| *A61K 31/496* | (2006.01) | |
| *A61K 9/19* | (2006.01) | |
| *A61K 47/34* | (2006.01) | |

(52) U.S. Cl.
CPC . *A61K 9/10* (2013.01); *A61K 9/19* (2013.01); *A61K 47/34* (2013.01)

(58) Field of Classification Search
None
See application file for complete search history.

(56) References Cited

U.S. PATENT DOCUMENTS

| | | |
|---|---|---|
| 4,225,456 A | 9/1980 | Schmidt et al. |
| 4,234,585 A | 11/1980 | Winter et al. |
| 5,006,528 A | 4/1991 | Oshiro et al. |
| 5,518,711 A | 5/1996 | Tonariya et al. |
| 2008/0039441 A1 | 2/2008 | Oberegger et al. |
| 2010/0015195 A1* | 1/2010 | Jain ............... A61K 9/0024 424/422 |
| 2010/0222435 A1* | 9/2010 | Oberegger et al. .......... 514/649 |

FOREIGN PATENT DOCUMENTS

| | | |
|---|---|---|
| EP | 0 006 506 A1 | 1/1980 |
| JP | 6-116170 A | 4/1994 |
| JP | 2002-114674 A | 4/2002 |
| JP | 2003-81882 A | 3/2003 |
| JP | 2006-316052 A | 11/2006 |
| JP | 2007-509148 A | 4/2007 |
| JP | 2007-509153 A | 4/2007 |
| JP | 2010-13364 A | 1/2010 |
| RU | 2342927 C2 | 1/2009 |
| WO | 2005/016261 A2 | 2/2005 |
| WO | 2005/032569 A1 | 4/2005 |
| WO | 2005/041937 A2 | 5/2005 |
| WO | 2005/041970 A1 | 5/2005 |
| WO | 2005/044232 A1 | 5/2005 |
| WO | 2005/055968 A1 | 6/2005 |
| WO | 2007/035348 A2 | 3/2007 |
| WO | 2008/066899 A2 | 6/2008 |
| WO | 2009/017250 A1 | 2/2009 |

OTHER PUBLICATIONS

International Search Report for PCT/JP2011/069243 dated Nov. 9, 2011.
Roger Wayne Croswell, Suspension Polymerization for Preparation of Prolonged Release Dosage Forms, A Dissertation Presented to the Graduate Council of the University of Florida in Partial Fulfillment of the Requirements for the Degree of Doctor of Philosophy, Dec. 1972, pp. 6-7.
Russian Patent Office, Office Action issued on Apr. 14, 2014 in Russian Application No. 2013113033.

\* cited by examiner

*Primary Examiner* — Jessica Worsham
(74) *Attorney, Agent, or Firm* — Finnegan, Henderson, Farabow, Garrett & Dunner LLP

(57) ABSTRACT

A suspension and a cake composition are provided in which agglomeration of the active ingredient that is caused when silicone oil and/or silicone oil derivative is contained therein can be suppressed without a special treatment, such as sonication. The suspension contains, in a dispersion medium, an active ingredient of a specific mean primary particle size, and silicone oil and/or silicone oil derivative. The cake composition contains an active ingredient of a specific mean particle size, and silicone oil and/or silicone oil derivative.

9 Claims, No Drawings

SUSPENSION AND CAKE COMPOSITION CONTAINING CARBOSTYRYL DERIVATIVE AND SILICONE OIL AND/OR SILICONE OIL DERIVATIVE

TECHNICAL FIELD

The present invention relates to a suspension and a cake composition that contain silicone oil and/or silicone oil derivative in a specific amount, and a carbostyryl derivative as an active ingredient.

BACKGROUND ART

Pharmaceutical compositions are used in various forms. For example, when used in the forms of suspensions and cake compositions, pharmaceutical compositions contain, in addition to a medicament contained as an active ingredient, additives, such as a defoaming agent, an excipient, a suspending agent, a buffer, a bulking agent, a lubricant, a fluidizer, a disintegrant, a binder, a surfactant, a preservative, a flavoring agent, an odor improving agent, and a tonicity agent. The defoaming agent is added to suppress liquid foaming, and is commonly used for preparing pharmaceutical compositions of forms including suspensions and cake compositions (see, for example, JP-A-2002-114674, WO/2005/032569, and JP-A-2010-13364).

Silicone oil used as pharmaceutical compositions is used as bases and defoaming agents, and because of their foam-suppressing small surface tension and very low toxicity, silicone oil represents a particularly useful additive for pharmaceutical compositions (see, for example, Iyakuhin Tenkabutsu Jiten 2007, International Pharmaceutical Excipients Council Japan, Jul. 25, 2007, p. 143, and JP-A-6-116170 and JP-A-2003-81882).

Aripiprazole, which is used as an active ingredient in pharmaceutical compositions, has the following structural formula (I):

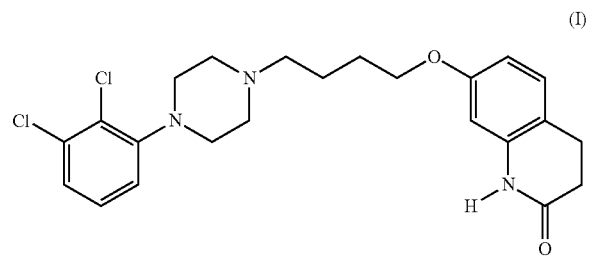 [SMILES: O=C1CCc2ccc(OCCCCN3CCN(c4cccc(Cl)c4Cl)CC3)cc2N1]

(I)

Aripiprazole is known as an atypical antipsychotic useful for the treatment of schizophrenia (U.S. Pat. No. 5,006,528).

Furthermore, a compound (7-[4-(4-benzo[b]thiophen-4-yl-piperazin-1-yl)butoxy]-1H-quinolin-2-one) represented by structural formula (II):

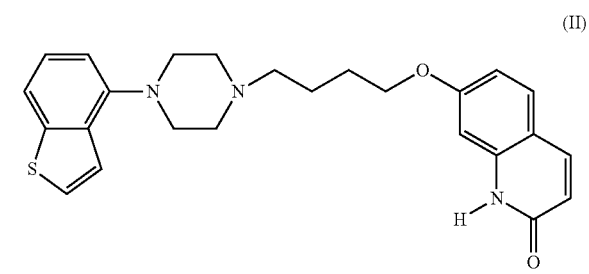 [SMILES: O=c1ccc2ccc(OCCCCN3CCN(c4cccc5sccc45)CC3)cc2[nH]1]

(II)

which is used as an active ingredient in pharmaceutical compositions is also known as an atypical antipsychotic useful for the treatment of schizophrenia (JP-A-2006-316052).

SUMMARY OF INVENTION

Technical Problem

However, it has been found that, in suspensions or cake compositions that contain, as an active ingredient, aripiprazole or a compound represented by structural formula (II) (hereunder refereed to as Compound (II)), which are known as atypical antipsychotics:

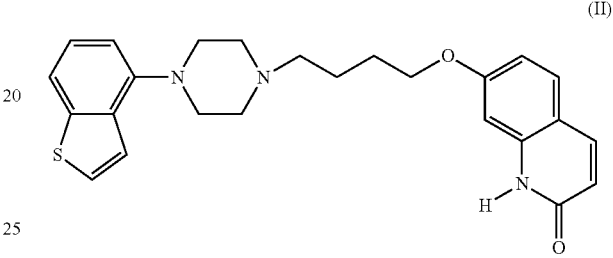

(II)

other additives may have adverse effects on the active ingredient contained therein, and that silicone oils and silicone oil derivatives contained in additives such as bases and defoaming agents have an agglomerating action on the active ingredient. When agglomeration occurs, the contacted areas of the active ingredient particles do not contribute to dissolving the particles, and this tends to lower the rate of dissolution. When the rate of dissolution changes, the blood concentration profile differs from that when the active ingredients are not agglomerated, and this has a considerable influence on the efficacy of the pharmaceutical composition. Therefore, when used in forms such as suspensions and cake compositions, aripiprazole and Compound (II) pose a problem in that they are unable to sufficiently exhibit their efficacy.

Furthermore, when used in an injection form, agglomeration of the active ingredients causes clogging, or an increased physical stimulus at the injection site due to increased particle size.

Solution to Problem

The present inventors conducted intensive studies to solve the foregoing problems, and found that the agglomeration of active ingredients could be suppressed without a special treatment, such as sonication, when the amount of silicone oil and/or silicone oil derivative contained in a suspension or cake composition that contains aripiprazole or Compound (II) as an active ingredient is set to a specific range. The present invention was completed by further studies based on this finding.

The present invention based on this finding includes the following.

Item 1. A method for preventing active ingredient particles from agglomerating in a suspension;
the suspension containing an active ingredient and silicone oil and/or silicone oil derivative in a dispersion medium;
the active ingredient being at least one member selected from the group consisting of aripiprazole and a compound represented by structural formula (II):

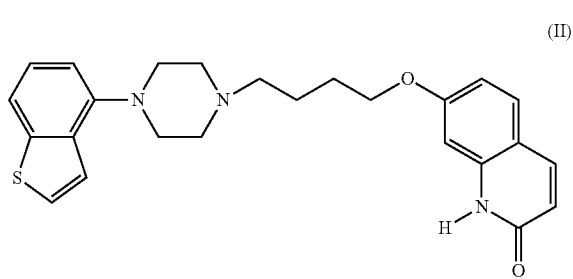 [SMILES: O=c1ccc2ccc(OCCCCN3CCN(c4cccc5sccc45)CC3)cc2[nH]1]

the active ingredient being in a form of particles having a mean primary particle size of 0.1 µm or larger and smaller than 200 µm;

the method comprising mixing the active ingredient with the silicone oil and/or silicone oil derivative in a dispersion medium, in such a manner that the silicone oil and/or silicone oil derivative is contained in an amount of 0.001 to 0.2 weight parts relative to 100 weight parts of the active ingredient contained in the suspension.

Item 2. The method for preventing the active ingredient particles from agglomerating in the suspension according to Item 1, wherein the active ingredient is aripiprazole.

Item 3. The method for preventing the active ingredient particles from agglomerating in the suspension according to Item 1, wherein the active ingredient is the compound represented by structural formula (II):

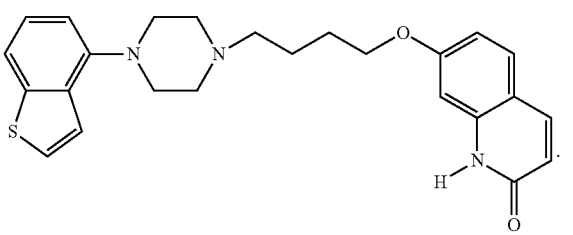

Item 4. A suspension comprising an active ingredient and silicone oil and/or silicone oil derivative in a dispersion medium; the active ingredient being at least one member selected from the group consisting of aripiprazole and a compound represented by structural formula (II):

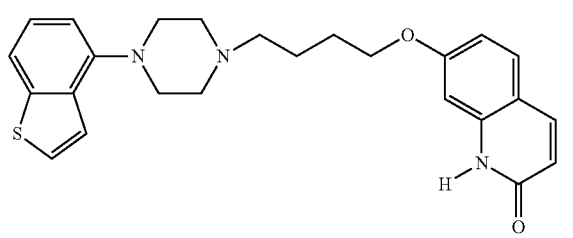

the active ingredient being in a form of particles and having a mean primary particle size of 0.1 µm or larger and smaller than 200 µm; and the silicone oil and/or silicone oil derivative being contained in an amount of 0.001 to 0.2 weight parts relative to 100 weight parts of the active ingredient contained in the suspension.

Item 5. The suspension according to Item 4, wherein the active ingredient is aripiprazole.

Item 6. The suspension according to Item 4, wherein the active ingredient is the compound represented by structural formula (II):

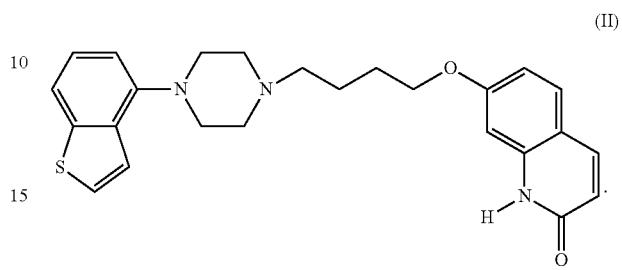

Item 7. A cake composition comprising an active ingredient and silicone oil and/or silicone oil derivative; the active ingredient being at least one member selected from the group consisting of aripiprazole and a compound represented by structural formula (II):

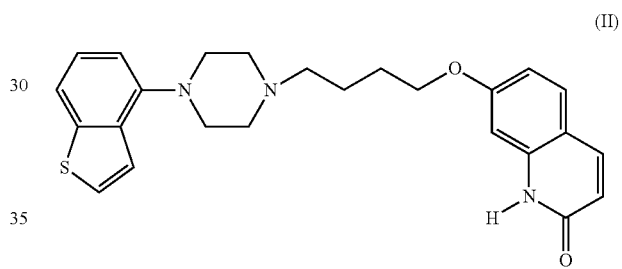

the active ingredient being in a form of particles and having a mean particle size of 0.1 µm or larger and smaller than 200 µm; and the silicone oil and/or silicone oil derivative being contained in an amount of 0.001 to 0.2 weight parts relative to 100 weight parts of the active ingredient contained in the cake composition.

Item 8. The cake composition according to Item 7, wherein the active ingredient is aripiprazole.

Item 9. The cake composition according to Item 7, wherein the active ingredient is the compound represented by structural formula (II):

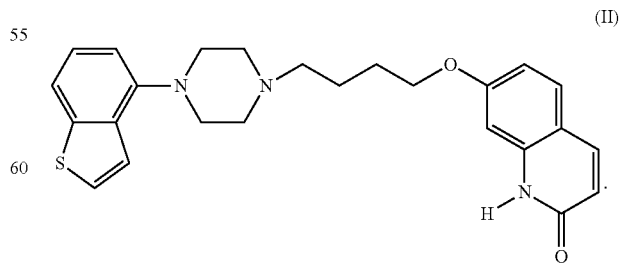

The following specifically describes the suspension and the cake composition of the present invention.

1. Suspension

The suspension of the present invention contains a specific active ingredient of a specific mean particle size, and silicone oil and/or silicone oil derivative in a dispersion medium (liquid medium).

The active ingredient is at least one member selected from the group consisting of aripiprazole and Compound (II).

1-1. Suspension Containing Aripiprazole as Active Ingredient

The content of silicone oil and/or silicone oil derivative is about 0.001 to 0.2 weight parts, preferably about 0.005 to 0.2 weight parts, more preferably about 0.01 to 0.2 weight parts, and still more preferably about 0.01 to 0.1 weight parts relative to 100 weight parts of aripiprazole. With the silicone oil and/or silicone oil derivative contained in these specific ranges, agglomeration of the aripiprazole particles in the suspension can be suppressed.

The silicone oil is one used in known medical applications, specifically, a linear polymer having a siloxane bond backbone with side chain alkyl groups of 1 to 6 carbon atoms. More specifically, the silicone oil may be one with the repeating unit represented by the following formula (1).

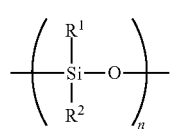

(1)

In formula (1), R1 and R2 are the same or different, and each represents a hydrogen atom or a hydrocarbon group of 1 to 6 carbon atoms, where n is an integer of 1 to 1,000.

Specific examples of the hydrocarbon group represented by R1 and R2 include a methyl group, an ethyl group, a propyl group, a butyl group, a pentyl group, and a hexyl group.

When n is 2 or more, the repeating units may be the same or different.

Specific examples of the silicone oil include dimethyl polysiloxane, and, in particular, dimethyl polysiloxane having a trimethylsilyl group on its terminals.

The silicone oil derivative may be one in which the substituent on side chain of the silicone oil, and/or some of the terminal Si substituents are replaced with, for example, a polyoxyalkylene group or a vinyl group.

The silicone oil and silicone oil derivative can be obtained from commercially available products, for example, Shin-Etsu Silicones KM72 and KF96ADF, both available from Shin-Etsu Chemical Co., Ltd., and Dow Corning® (produced by Dow Corning Corporation). Emulsion (Dow Corning® 365, 35% Dimethicone NF Emulsion (produced by Dow Corning Corporation)), which contains a surfactant and water, can also be used as the silicone oil.

The average molecular weight of the silicone is not particularly limited, and is preferably from 10 to 100,000,000, more preferably from 100 to 10,000,000, and still more preferably from 200 to 10,000.

The dispersion medium used for the suspension of the present invention includes water, an aqueous solvent containing water and an organic solvent, etc., and sterile water (distilled water). The organic solvent is one that is miscible with water. Examples include alcohols, such as methanol, ethanol, propanol, and isopropanol; ketones such as acetone; ethers such as tetrahydrofuran; dimethylformamide; and mixtures thereof. Of these, ethanol is particularly preferred.

The amount of water used for the aqueous solvent is not particularly limited, and is, for example, preferably at least 10 weight % of the solvent.

The mean primary particle size of the aripiprazole in the suspension is preferably 0.1 µm or larger, more preferably 0.5 µm or larger, and still more preferably 1.5 µm or larger in sustained-release injections, because a sustained release lasting as long as 1 month can be desirably obtained with these ranges. From the standpoint of slowing settling, improving ease of manufacture, and preventing needle clogging during injections, the mean primary particle size of the aripiprazole in the suspension is preferably smaller than 200 µm, more preferably smaller than 10 µm, still more preferably from about 2 to about 4 µm, and most preferably about 2.5 µm.

Here, the "mean particle size" means a volume mean diameter as measured by a laser diffraction scattering method. The particle distribution is measured using a laser diffraction scattering method, and is used for the calculation of mean particle size. The term "primary particle size" means the particle size of each individual particle, not the particle size of agglomerated particles. The "mean primary particle size" means the mean particle size of the primary particles.

Aripiprazole with the desired mean primary particle size can be produced by using preferably, for example, an impinging jet crystallization method (see JP-T-2007-509153 filed by Bristol-Myers Squibb), or a wet pulverization method that uses a high-pressure homogenizer (see Japanese Patent Application No. 2007-200088 filed by Otsuka Pharmaceutical Co., Ltd.).

Aripiprazole in a suspension is known to exist in a variety of crystal forms, including monohydrates (aripiprazole hydrate A), and many anhydrous forms, specifically, such as anhydrous crystal B, anhydrous crystal C, anhydrous crystal D, anhydrous crystal E, anhydrous crystal F, and anhydrous crystal G. All of these forms may be used in the preparation of the present invention.

From the standpoint of reducing the dose as much as possible, the solids content of the aripiprazole in the suspension is preferably about 1 weight % or more, more preferably about 5 weight % or more, and still more preferably about 10 weight % or more. Further, in terms of fluidity and the desired viscosity for smooth passage through a needle, the solids content of the aripiprazole in the suspension is preferably about 40 weight % or less, more preferably about 35 weight % or less, and still more preferably about 30 weight % or less.

The suspension of the present invention may also appropriately contain other components, such as a suspending agent, a bulking agent, a buffer, a pH adjuster, an excipient, a lubricant, a fluidizer, a disintegrant, a binder, a surfactant, a preservative, a flavoring agent, an odor improving agent, and a tonicity agent, in addition to aripiprazole, silicone oil and/or silicone oil derivative, and a dispersion medium.

The additives may be those described in JP-T-2007-509148.

The content of the suspending agent is preferably about 0.2 to 10 weight %, more preferably about 0.5 to 5 weight % relative to the total weight of the suspension. The suspending agent may be selected from sodium carboxymethylcellulose, hydroxypropylcellulose, carboxymethylcellulose, hydroxypropylethylcellulose, hydroxypropylmethylcellulose, and polyvinylpyrrolidone, or a mixture of two or more of these. However, the suspending agent is not limited to these, and sodium carboxymethylcellulose and polyvinylpyrrolidone can preferably be used.

Examples of other suspending agents suited for use as the vehicle of the aripiprazole include various polymers, low molecular oligomers, natural products, and surfactants (both nonionic and ionic).

Specific examples include cetylpyridinium chloride, gelatin, casein, lecithin (phosphatide), dextran, glycerol, gum acacia, cholesterol, tragacanth, stearic acid, benzalkonium chloride, calcium stearate, glyceryl monostearate, cetostearyl alcohol, cetomacrogol emulsifying wax, sorbitan ester, polyoxyethylenealkyl ether (for example, amacrogol ether such as cetomacrogol 1000), a polyoxyethylene castor oil derivative, a polyoxyethylenesorbitan fatty acid ester (for example, commercially available Tweens®, including Tween20® and Tween80® (ICI Specialty Chemicals)).

Other examples include polyethylene glycols (for example, Carbowaxes 3350® and 1450®, and Carbopol 934® (Union Carbide)), dodecyltrimethylammonium bromide, polyoxyethylene stearate, colloidal silicon dioxide, phosphate, sodium dodecyl sulfate, carboxymethylcellulose calcium, hydroxypropylcellulose (for example, HPC, HPC-SL, and HPC-L), methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), ethylene oxide-formaldehyde 4-(1,1,3,3-tetramethylbutyl)-phenol polymers (also known as tyloxapol, superione, and triton), poloxamers (for example, Pluronics F68® and F108®, which are block copolymers of ethylene oxide and propylene oxide); poloxamine (also known as, for example, Tetronic 908® and Poloxamine908®, which are tetrafunctional block copolymers derived from the continuous addition of propylene oxide and ethylene oxide to ethylenediamine (produced by BASF Wyandotte Corporation, Parsippany, N.J.); charged phospholipids, such as dimyristoylphosphatidylglycerol and dioctylsulfosuccinate (DOSS); Tetronic 1508® (T-1508; produced by BASF Wyandotte Corporation), dialkyl esters of sodium sulfosuccinate (for example, Aerosol OT®, which is a dioctyl ester of sodium sulfosuccinate (produced by American Cyanamid)); Duponol P® (a sodium lauryl sulfate; produced by DuPont); Tritons X-200® (an alkylarylpolyether sulfonate; produced by Rohm and Haas); Crodestas F-110® (a mixture of sucrose stearate and sucrose distearate; produced by Croda Inc.); p-isononylphenoxypoly-(glycidol) (also known as Olin-10G® or Surfactant 10-G® (Olin Chemicals, Stamford, Conn.)); Crodestas SL-40® (produced by Croda, Inc.); SA9OHCO (C18H37CH2(CON(CH3))—CH2(CHOH)4 (CH2OH)2 (produced by Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; and octyl β-D-thioglucopyranoside.

Most of these suspending agents are known pharmaceutical excipients, and are described in detail in the Handbook of Pharmaceutical Excipients, co-published by the American Pharmaceutical Association and The Pharmaceutical Society of Great Britain (The Pharmaceutical Press, 1986), which is specifically incorporated herein by reference. The suspending agents are commercially available, and can be produced by techniques known in the art.

The content of the bulking agent (also called a cryogenic/lyophilize protecting agent) is preferably about 1 to 20 weight %, more preferably about 2 to 10 weight %, and still more preferably about 3 to 8 weight % relative to the total weight of the suspension. The bulking agent may be selected from, for example, mannitol, sucrose, maltose, xylitol, glucose, starch, and sorbitol, or a mixture of two or more of these. However, the bulking agent is not limited to these, and mannitol can be preferably used.

The buffer is used in an amount that adjusts the suspension pH to about 6 to 8, and preferably about 7. In order to attain such a pH, the buffer content typically falls within a range of preferably about 0.02 to 2 weight %, more preferably about 0.03 to 1 weight %, and still more preferably about 0.1 weight % relative to the total weight of the suspension, depending on the type of buffer used.

The preferred buffer may be selected from, for example, sodium phosphate, sodium hydrogenphosphate, disodium hydrogenphosphate, potassium phosphate, and TRIS buffer, or a mixture of two or more of these. However, the buffer is not limited to these, and sodium phosphate, sodium hydrogenphosphate, and disodium hydrogenphosphate are preferably used.

The pH adjuster is used in an amount that adjusts the pH of the aripiprazole aqueous suspension to about 6 to 7.5, preferably about 7. The pH adjuster is either an acid or a base, depending on whether the pH of the freeze-dried aripiprazole aqueous suspension needs to be raised or lowered to achieve the desired neutral pH of about 7. When the pH needs to be lowered, an acidic pH adjuster, such as hydrochloric acid, acetic acid, or preferably hydrochloric acid is used. When the pH needs to be raised, a basic pH adjuster, such as sodium hydroxide, potassium hydroxide, calcium carbonate, magnesium oxide, or magnesium hydroxide, or preferably sodium hydroxide is used.

The method used to prepare the suspension of the present invention is not particularly limited. For example, the suspension is prepared by mixing the aripiprazole, predetermined amounts of the silicone oil and/or silicone oil derivative, a dispersion medium, and, optionally, additives. Preferably, a wet pulverization technique is used, and the dispersed aripiprazole particles are subjected to pulverization in the presence of a pulverization medium to have a desired mean primary particle size.

Preferably, an antiseptic wet pulverization technique, such as wet ball milling, high pressure homogenization, and high shear homogenization is used. In addition to these pulverization techniques, a low-energy or high-energy mill (for example, a roller mill) can also be used.

Use of, for example, controlled crystallization is also possible.

It is possible to prevent active ingredient particles contained in a suspension from agglomerating by mixing the active ingredient with the silicone oil and/or silicone oil derivative in a dispersion medium. The content of the silicone oil and/or silicone oil derivative are the same as those mentioned above.

A homogeneous suspension of aripiprazole having a desired mean primary particle size free from agglomeration can be obtained by using the above-mentioned methods.

1-2. Suspension Containing Compound (II) as Active Ingredient

The present invention also relates to a suspension containing Compound (II) having a specific mean primary particle size in a dispersion medium, and silicone oil and/or silicone oil derivative.

In the same manner as the suspension containing aripiprazole represented by structural formula (I) described above, a suspension containing Compound (II) exhibits similar effects.

The mean primary particle size of Compound (II) in the suspension is preferably 0.1 μm or larger. From the standpoint of slowing settling, improving ease of manufacture, and preventing needle clogging during injections, the mean primary particle size of Compound (II) in the suspension is preferably smaller than 200 μm.

Here, the "mean primary particle size" means the same as described above.

The content of the silicone oil and/or silicone oil derivative is about 0.001 to 0.2 weight parts, preferably about 0.005 to 0.2 weight parts, more preferably about 0.01 to 0.2 weight parts, and still more preferably about 0.01 to 0.1 weight parts relative to 100 weight parts of Compound (II). With the silicone oil and/or silicone oil derivative contained in these specific ranges, agglomeration of Compound (II) in the suspension can be suppressed.

Specific examples of the silicone oil and/or silicone oil derivative are the same as those mentioned above.

The dispersion medium used for the suspension is water, or an aqueous solvent containing water and an organic solvent. The organic solvents mentioned above are also usable here. Ethanol is preferable as the organic solvent. The amount of water used for the aqueous solvent is not particularly limited, and is, for example, preferably at least 10 weight % of the solvent.

From the standpoint of reducing the dose as much as possible, the solids content of Compound (II) in the suspension is preferably about 1 weight % or more, more preferably about 5 weight % or more, and still more preferably about 10 weight % or more. Further, in terms of fluidity and the desired viscosity for smooth passage through a needle, the solids content of the Compound (II) in the suspension is preferably about 40 weight % or less, more preferably about 35 weight % or less, and still more preferably about 30 weight % or less.

The suspension of the present invention may also appropriately contain other components, such as a suspending agent, a bulking agent, a buffer, a pH adjuster, an excipient, a lubricant, a fluidizer, a disintegrant, a binder, a surfactant, a preservative, a flavoring agent, an odor improving agent, and a tonicity agent, in addition to Compound (II), silicone oil and/or silicone oil derivative, and a dispersion medium.

Specific examples of the additives and the amounts contained thereof are the same as those described above. The preferable examples of additives and the preferable amounts contained thereof are the same as those described above.

The method used to prepare the suspension of the present invention is not particularly limited. For example, the suspension is prepared by mixing Compound (II), predetermined amounts of the silicone oil and/or silicone oil derivative, a dispersant, and, optionally, additives.

It is possible to prevent active ingredient particles contained in a suspension from agglomerating by mixing the active ingredient with the silicone oil and/or silicone oil derivative in a dispersion medium. The content of the silicone oil and/or silicone oil derivative are the same as those mentioned above.

In the preparation, a wet pulverization technique mentioned above is usable. By employing the wet pulverization technique, a homogeneous suspension free from agglomeration comprising Compound (II) having a desired mean primary particle size can be obtained.

A suspension of the present invention that contains at least one active ingredient selected from the group consisting of aripiprazole and Compound (II) can be suitably used for, for example, injections, oral liquid medicines, and injections and oral liquid medicines suspended at the time of use.

2. Cake Composition

The cake composition of the present invention contains a specific active ingredient and silicone oil and/or silicone oil derivative.

As used herein, the "cake" in the cake composition means a dried solid that maintains the shape of the liquid before drying. For example, when a vial that has a columnar inner shape is used, the cake is a dried solid that maintains the columnar shape. The cake can be produced by, for example, freeze-drying the suspension of the present invention. Generally, a freeze-dried cake is brittle, and often cracks by physical impact that occurs during preservation. However, even cakes with such cracks caused by impact or other forces fall within the definition of a "cake," provided that such cracks occur after the production of the cake.

The aforementioned active ingredient means at least one member selected from the group consisting of aripiprazole and Compound (II).

2-1. Cake Composition Containing Aripiprazole as Active Ingredient

The silicone oil and/or silicone oil derivative is contained in an amount of about 0.001 to 0.2 weight parts, preferably about 0.005 to 0.2 weight parts, more preferably about 0.01 to 0.2 weight parts, and still more preferably about 0.01 to 0.1 weight parts relative to 100 weight parts of aripiprazole. With the silicone oil and/or silicone oil derivative contained in these specific ranges, the agglomeration of the aripiprazole during the dispersion of the cake composition in a dispersion medium can be suppressed.

The same silicone oil and silicone oil derivative specifically exemplified for the suspension can be used.

The mean particle size of the aripiprazole in the cake composition is preferably 0.1 μm or larger, more preferably 0.5 μm or larger, and still more preferably 1.5 μm or larger in sustained-release injections, because a sustained release lasting as long as 1 month can be desirably obtained with these ranges. From the standpoint of slowing settling, improving ease of manufacture, and preventing needle clogging during injections, the mean particle size of the aripiprazole in the cake composition is preferably smaller than 200 μm, more preferably smaller than 10 μm, still more preferably about 2 to 4 μm, and most preferably about 2.5 μm.

Note that the "mean particle size" can be measured using the same measurement method used for the suspension.

The aripiprazole for use in the cake composition can be prepared by the same method used to prepare the suspension containing aripiprazole. Further, the aripiprazole may be of the same crystal form contained in the suspension.

In addition to the aripiprazole and the silicone oil and/or silicone oil derivative, the cake composition of the present invention may also appropriately contain additives, such as a suspending agent, a bulking agent, a buffer, a pH adjuster, an excipient, a lubricant, a fluidizer, a disintegrant, a binder, a surfactant, a preservative, a flavoring agent, an odor improving agent, and a tonicity agent. The same additives specifically exemplified for the suspension can be used.

The method for preparing the cake composition of the present invention is not particularly limited. For example, the cake composition may be prepared by freeze-drying the suspension.

The cake composition of the present invention may be resuspended by adding the dispersion medium used to prepare the suspension. Examples of the dispersion medium used for this purpose include water (preferably, distilled water), a polymer aqueous solution, and a surfactant aqueous solution.

The suspension (resuspension) obtained by adding the dispersion medium to the cake composition as described above has the same constitution as that of the aforementioned suspension. This also allows a homogeneous suspension comprising aripiprazole with a desired mean primary particle size to be obtained without the formation of agglomeration.

2-2. Cake Composition Containing Compound (II) as Active Ingredient

The present invention also relates to a cake composition containing Compound (II) and silicone oil and/or silicone oil derivative.

The "cake" in the cake composition is defined as being the same as described above.

In the same manner as the cake composition containing aripiprazole represented by structural formula (I), a cake composition containing Compound (II) exhibits similar effects.

The mean primary particle size of Compound (II) in the cake composition is preferably 0.1 μm or larger. From the standpoint of slowing settling, improving ease of manufacture, and preventing needle clogging during injections, the mean particle size of Compound (II) in the cake composition is preferably smaller than 200 μm.

Note that "mean particle size" and "primary particle size" have the same meanings as described above.

The content of the silicone oil and/or silicone oil derivative is about 0.001 to 0.2 weight parts, preferably about 0.001 to 0.2 weight parts, more preferably about 0.01 to 0.2 weight parts, and still more preferably about 0.01 to 0.1 weight parts relative to 100 weight parts of Compound (II). With the silicone oil and/or silicone oil derivative contained in these specific ranges, the compound (II) in the suspension can be suppressed. Specific examples of the silicone oil and/or silicone oil derivative are the same as those mentioned above.

The method for preparing Compound (II) used in the cake composition may be the same as that for preparing the suspension.

In addition to Compound (II) and the silicone oil and/or silicone oil derivative, the cake composition of the present invention may also appropriately contain additives, such as a suspending agent, a bulking agent, a buffer, a pH adjuster, an excipient, a lubricant, a fluidizer, a disintegrant, a binder, a surfactant, a preservative, a flavoring agent, an odor improving agent, and a tonicity agent. Specific examples of the additives and the amounts contained thereof may be the same as those described above. Preferable examples and preferable amounts contained thereof may also be the same as those described above.

The method for preparing the cake composition of the present invention is not particularly limited. For example, the cake composition may be prepared by freeze-drying a suspension containing Compound (II).

The cake composition of the present invention may be resuspended by adding the dispersion medium used to prepare the suspension. The dispersion medium used for this purpose may be the same as described above. Preferable examples and preferable amounts of the dispersion medium contained are the same as those mentioned above.

The suspension (resuspension) obtained by adding the dispersion medium to the cake composition as described above has the same constituent as that of the aforementioned suspension, and a homogeneous suspension comprising compound (II) having a desired mean primary particle size without causing agglomeration of compound (II) can be obtained.

The cake composition of the present invention can be suitably used for, for example, oral liquid medicines and injections suspended at the time of use. When prepared as a suspension by being mixed with a dispersion medium, the cake composition can be suitably used as, for example, injections and oral liquid medicines.

Advantageous Effects of Invention

The suspension of the present invention can desirably disperse the particles of the active ingredient, i.e., aripiprazole or Compound (II), without causing agglomeration, despite the fact that additives, such as silicone oil and/or silicone oil derivative, are contained.

Further, the particles of aripiprazole or Compound (II) can be desirably dispersed without agglomeration when the cake composition of the present invention is dispersed in a dispersion medium, despite the fact that the cake composition contains silicone oil and/or silicone oil derivative that causes the particles of the active ingredient, i.e., aripiprazole or Compound (II), to agglomerate. The particles of aripiprazole or Compound (II) can thus be desirably dispersed without special treatment, such as sonication.

DESCRIPTION OF EMBODIMENTS

Examples

The following describes the present invention in more detail based on Examples and Comparative Examples. It should be noted, however, that the present invention is not limited to the following descriptions.

Examples 1 to 2 and Comparative Examples 1 to 4

Suspensions containing aripiprazole and silicone oil in the contents presented in Table 1 were prepared according to the following method. A 0.1% or 1% silicone oil emulsion prepared by diluting Dow Corning® 365, 35% Dimethicone NF Emulsion (produced by Dow Corning Corporation) in purified water was used as the silicone oil. A sodium carboxymethylcellulose/mannitol/sodium dihydrogenphosphate solution was used as a dispersion medium. The solids content of the aripiprazole was adjusted to about 10 to 20 weight %. No foaming occurred in any of the suspensions.

Suspension Preparation Method

An aqueous suspension (200 mg aripiprazole/1.1 to 2 mL) containing aripiprazole (IM Depot) and silicone oil was prepared as follows.

Note that the aripiprazole suspension was prepared according to a wet pulverization method that uses a high-pressure homogenizer (see Japanese Patent Application No. 2007-200088 filed by Otsuka Pharmaceutical Co., Ltd.).

An aripiprazole hydrate bulk powder was suspended in a dispersion medium at 20 weight %. The concentrations of other additives dissolved in the suspension were about 0.83 weight % sodium carboxymethylcellulose, about 4.2 weight % mannitol, and about 0.074 weight % sodium dihydrogenphosphate monohydrate. The pH was adjusted to about 7 with a sodium hydroxide aqueous solution. The suspension was preliminarily pulverized with a high shear rotary homogenizer (Clearmix; produced by M Technique Co., Ltd.), and then repeatedly wet pulverized with a high-pressure homogenizer (produced by Niro) at 550 bar. The mean primary particle size of the resulting suspension was 2.0 μm. The silicone oil emulsion (0.1 to 1 mL) diluted to 0.1% or 1% was then added to 1 mL of the suspension to obtain an aqueous suspension that contained aripiprazole (IM Depot) and silicone oil.

The mean particle size of the suspension prepared as described above was measured using a SALD-3000J or SALD-3100 Laser Diffraction Particle Size Analyzer (produced by Shimadzu Corporation). The measurement was made at a refractive index of 2.00 to 0.20i, using water as the measurement medium in a circulation cell.

Separately, the suspension was sonicated for 1 min with an ultrasonic wave generator attached to the particle size analyzer, and the mean particle size of the treated suspension was measured as described above. Table 1 shows the measurement results.

TABLE 1

| | | Example | | Comparative Example | | | |
|---|---|---|---|---|---|---|---|
| | | 1 | 2 | 1 | 2 | 3 | 4 |
| Components (Suspension) (weight parts) | Aripiprazole | 100 | 100 | 100 | 100 | 100 | 100 |
| | Silicone oil | 0.05 | 0.1 | 0.5 | 1 | 2.5 | 5 |
| Mean particle size (μm) | No ultrasonic treatment | 2.2 | 2.6 | 5.6 | 13.2 | 18.1 | 23.1 |
| | Ultrasonic treatment | 2.1 | 2.0 | 2.2 | 2.7 | 6.8 | 10.2 |
| | Difference (no ultrasonic treatment-ultrasonic treatment) | 0.1 | 0.6 | 3.4 | 10.5 | 11.3 | 12.9 |

Discussion

It can be seen in Table 1 that the aripiprazole mean particle size does not differ greatly before and after the sonication in Examples 1 and 2. The difference was only 0.1 μm in Example 1 in which the silicone oil was contained at 0.05 weight parts relative to 100 weight parts of aripiprazole, and only 0.6 μm in Example 2 in which the silicone oil content was 0.1 weight parts. The results thus demonstrated that aripiprazole was desirably dispersed without agglomerating, and the homogeneous suspension was obtained.

On the other hand, the mean particle size of aripiprazole was relatively large, i.e., 5.6 μm, before sonication in Comparative Example 1, which contained 0.5 weight parts of silicone oil relative to 100 weight parts of aripiprazole, and it was reduced to 2.2 μm after the sonication. Because of the fact that sonication reduced the mean particle size, it became clear that agglomeration occurred in the aripiprazole that was present in the suspension of Comparative Example 1, and that the aripiprazole could not be dispersed without special treatment, such as sonication. In Comparative Examples 2 to 4, which contained silicone oil in 1 to 5 weight parts, the aripiprazole had very large mean particle sizes of 13.2 to 23.1 μm before sonication. The sonication reduced the mean particle size to 2.7 to 10.2 μm; however, the agglomeration was so strong that sonication was not sufficient to restore the original particle size of about 2.0 μm. These results thus demonstrated that agglomeration becomes more severe with increases in the silicone amount.

Examples 3 and 4

The cake compositions of Examples 3 and 4 containing aripiprazole and silicone oil in the contents presented in Table 3 were prepared from a dried, silicone oil-free cake by having it absorb the silicone oil in a later step as described below. The same aripiprazole and silicone oil used in Example 1 were used.

Cake Composition Preparation Method

An aripiprazole (IM Depot) aqueous suspension (300 mg aripiprazole/mL was prepared according to the method of Example 1. A 0.5% or 5% silicone oil emulsion prepared by diluting Dow Corning® 365, 35% Dimethicone NF Emulsion (produced by Dow Corning Corporation) in purified water was applied to the inner surface of a glass tube (φ14.0×106 mm). The glass tube was baked at about 300° C. for at least 10 min to evaporate the water in the emulsion and to thereby obtain a silicone-treated glass tube. Table 2 shows the amount of silicone oil per 100 mm2.

The silicone oil applied to the glass inner surface was quantified by washing the inner surface of the glass tube with methyl isobutyl ketone, and then by measuring the solution using an atomic absorption spectrometer with an Si measurement lamp under the following conditions.

Measurement wavelength: 251.6 nm
Drying: From 50° C. to 80° C., 40 sec
Ashing: 1,000° C., 20 sec
Atomization: 2,700° C., 5 sec
Cleaning: 2,800° C., 15 sec
Cooling: 17 sec One end of the glass tube was capped with a rubber plug, and the aripiprazole suspension (about 1.5 mL) was inserted into the tube. The glass tube containing the aripiprazole suspension was transferred to a freeze-dryer, and freeze-dried in the following cycle to obtain a cake composition.

(a) Thermal treatment: The product was frozen for about 3 hours at a temperature that was maintained at about −40° C.

(b) Primary drying: Primary drying was continued for at least 20 hours under increased chamber pressure (about 13 Pa) and increased shelf temperature (about −5° C.).

The cake composition obtained as described above containing about 450 mg of aripiprazole maintained the same liquid level as it was inserted into the glass tube and was in contact with the glass surface. Because this made the removal of the cake composition difficult, the cake composition was gently broken into several pieces with a medicine spoon, removed from the glass tube, and placed into a vial that had not been treated with silicone. After adding 2 mL of a dispersion medium (water), the vial was vigorously shaken by hand to prepare a resuspension liquid. The mean particle size of the resulting suspension was measured according to the method of Example 1. The amount of silicone in the suspension was measured by extracting the resuspension liquid with methyl isobutyl ketone, and then by measuring the methyl isobutyl ketone solution with an atomic absorption spectrometer. There was no foaming in either suspension.

The suspension was sonicated for 1 min with the ultrasonic device used in Example 1, and the mean particle size of the treated suspension was measured as described above as described above. Table 3 shows the measurement results.

Examples 5 and 6

The cake compositions of Examples 5 and 6 containing aripiprazole and silicone oil in the contents presented in Table 3 were prepared according to the following method. The same aripiprazole and silicone oil used in Example 1 were used.

Cake Composition Preparation Method

An aripiprazole (IM Depot) aqueous suspension (300 mg aripiprazole/mL) was prepared according to the method of Example 1. A 1% silicone oil emulsion was prepared by diluting Dow Corning® 365, 35% Dimethicone NF Emulsion (produced by Dow Corning Corporation) in purified water. Then, an aripiprazole and silicone oil aqueous suspension was prepared by adding 0.2 mL (silicone oil 2 mg) of the silicone emulsion to 15 mL (aripiprazole 4.5 g) or 6 mL (aripiprazole 1.8 g) of the aripiprazole suspension.

About 1.5 mL of the suspension was placed in a glass vial that had not been treated with silicone, and transferred to a freeze-dryer. The suspension was freeze-dried according to the following cycle to obtain a cake composition.

(a) Thermal treatment: The product was frozen for about 3 hours at a temperature that was maintained at about −40° C.

(b) Primary drying: Primary drying was continued for at least 20 hours under increased chamber pressure (about 13 Pa) and increased shelf temperature (about −5° C.).

After adding 2 mL of a dispersion medium (water), the freeze-dried cake obtained as described above was vigorously shaken by hand to obtain a resuspension liquid. The mean particle size of the resulting suspension was measured according to the method of Example 1. There was no foaming in either suspension.

The suspension was sonicated for 1 min with the ultrasonic device used in Example 1, and the mean particle size of the treated suspension was measured as described above. Table 3 shows the measurement results.

Comparative Examples 5 and 6

The cake composition of Comparative Example 5 containing aripiprazole and silicone oil in the contents presented in Table 3 was prepared according to the following method. The same aripiprazole and silicone oil used in Example 1 were used.

Cake Composition Preparation Method

An aripiprazole (IM Depot) aqueous suspension (300 mg aripiprazole/mL) was prepared according to the method of Example 1. A 1% silicone oil emulsion was prepared by diluting Dow Corning® 365, 35% Dimethicone NF Emulsion (produced by Dow Corning Corporation) in purified water. Then, an aripiprazole and silicone oil aqueous suspension was prepared by adding 1.5 mL (aripiprazole 450 mg) of the aripiprazole suspension and 0.5 mL (silicone oil 5 mg) or 1 mL (silicone oil 10 mg) of the silicone emulsion to a glass vial that had not been treated with silicone.

The glass vial was transferred to a freeze-dryer, and freeze-dried according to the following cycle to obtain a cake composition.

(a) Thermal treatment: The product was frozen for about 3 hours at a temperature that was maintained at about −40° C.

(b) Primary drying: Primary drying was continued for at least 20 hours under increased chamber pressure (about 13 Pa) and increased shelf temperature (about −5° C.).

After adding 2 mL of a dispersion medium (water), the freeze-dried cake of Comparative Example 5 obtained as described above was vigorously shaken by hand to obtain a resuspension liquid. The mean particle size of the resulting suspension was measured according to the method of Example 1. There was no foaming in either suspension. After adding 2 mL of a dispersion medium (water), Comparative Example 6 obtained as described above was vigorously shaken by hand, however, the freeze-dried cake of Comparative Example 6 severely agglomerated, and could not be resuspended.

The resuspension of Comparative Example 5 was sonicated for 1 min with the ultrasonic device used in Example 1, and the mean particle size of the treated suspension was measured as described above. Table 3 shows the measurement results.

TABLE 2

| Applied emulsion concentration | Silicone amount on glass inner surface per 100 mm2 |
| --- | --- |
| 5% | 11 μg |
| 0.5% | 1 μg |

TABLE 3

| | | Example | | | | Comparative Example | |
| --- | --- | --- | --- | --- | --- | --- | --- |
| | | 3 | 4 | 5 | 6 | 5 | 6 |
| Applied emulsion concentration on inner surface of glass tube | | 0.5% | 5% | — | — | — | — |
| Components (Cake composition) (weight parts) | Aripiprazole | 100 | 100 | 100 | 100 | 100 | 100 |
| | Silicone oil | 0.019 | 0.024 | 0.044 | 0.11 | 1.1 | 2.2 |
| Mean particle size (μm) | No ultrasonic treatment | 2.5 | 2.8 | 2.5 | 3.2 | 9.9 | * |
| | Ultrasonic treatment | 2.3 | 2.3 | 2.1 | 2.1 | 3.3 | * |
| | Difference (no ultrasonic treatment-ultrasonic treatment) | 0.2 | 0.5 | 0.4 | 1.1 | 6.6 | — |

*Agglomeration was so severe that redispersion and measurement were not possible.

Discussion

It can be seen in Table 3 that the aripiprazole mean particle size does not differ greatly before and after sonication in Examples 3 to 6. The difference was only 0.2 to 1.1 μm in Examples 3 to 6, in which the silicone oil was contained in 0.01 to 0.2 weight parts relative to 100 weight parts of aripiprazole. The results thus demonstrated that aripiprazole was desirably dispersed without agglomerating in the suspensions of Examples 3 to 6, in which the cake compositions were dispersed in the dispersion medium.

On the other hand, the aripiprazole mean particle size before sonication was very large, i.e., 9.9 μm or higher, in Comparative Examples 5 and 6, which contained 1.1 to 2.2 weight parts of silicone oil relative to 100 weight parts of aripiprazole, and the difference of the aripiprazole mean particle size before and after sonication was as large as 6.6 μm. Notably, in Comparative Example 6, which contained 2.2 weight parts of silicone oil relative to 100 weight parts of aripiprazole, agglomeration was so severe that the aripiprazole could not be redispersed.

The foregoing results demonstrate that the agglomerated aripiprazole cannot be dispersed without a specific treatment such as sonication. Further, by comparing Examples 3 to 6 and Comparative Examples 5 to 6, it can be seen that the aripiprazole agglomeration in the suspension is dependent on the content of the silicone oil in the cake composition.

Examples 7 to 9 and Comparative Examples 7 to 10

Suspensions containing Compound (II) and silicone oil in the contents presented in Table 4 were prepared according to the following method. A 0.1% or 1% silicone oil emulsion prepared by diluting Dow Corning® 365, 35% Dimethicone NF Emulsion (produced by Dow Corning Corporation) in purified water was used as the silicone oil. A sodium carboxymethylcellulose/mannitol/sodium dihydrogenphosphate solution was used as a dispersion medium. The solids content of Compound (II) was adjusted to 10 to 20 weight %. No foaming occurred in any of the suspensions.

Suspension Preparation Method

An aqueous suspension (200 mg Compound (II)/1.1 to 2 mL) containing Compound (II) and silicone oil was prepared as follows. Note that the Compound (II) suspension was prepared in the same manner as in Example 1 except that the pulverizing time using a high-pressure homogenizer was shortened.

A Compound (II) bulk powder was suspended in a dispersion medium at 20 weight %. The dispersion medium that was used had the same concentrations of other additives as those of the dispersion medium used in Example 1, i.e., about 0.83 weight % sodium carboxymethylcellulose, about 4.2 weight % mannitol, and about 0.074 weight % sodium dihydrogenphosphate monohydrate. The pH was adjusted to about 7 with a sodium hydroxide aqueous solution. The suspension was preliminarily pulverized with a high shear rotary homogenizer (Clearmix; produced by M Technique Co., Ltd.), and then wet pulverized with a high-pressure homogenizer (produced by Niro) at 550 bar. The mean primary particle size of the resulting suspension was 5.3 μm. A silicone oil emulsion (0.1 to 1 mL) diluted to 0.1% or 1% was then added to 1 mL of the suspension to obtain an aqueous suspension that contained Compound (II) and silicone oil.

The mean particle size of the suspension prepared as described above was measured using a SALD-3000J or SALD-3100 Laser Diffraction Particle Size Analyzer (produced by Shimadzu Corporation). The measurement was made at a refractive index of 2.00 to 0.20i, using water as the measurement medium in a circulation cell.

Separately, the suspension was sonicated for 1 min with an ultrasonic wave generator attached to the particle size analyzer, and the mean particle size of the treated suspension was measured as described above. Table 4 shows the measurement results.

TABLE 4

| | | Example | | | Comparative Example | | | |
|---|---|---|---|---|---|---|---|---|
| | | 7 | 8 | 9 | 7 | 8 | 9 | 10 |
| Components (Suspension) (weight parts) | Compound (II) | 100 | 100 | 100 | 100 | 100 | 100 | 100 |
| | Silicone oil | 0.025 | 0.05 | 0.1 | 0.5 | 1 | 2.5 | 5 |
| Mean particle size (μm) | No ultrasonic treatment | 5.4 | 6.0 | 6.3 | 9.8 | 14.4 | 19.8 | 15.9 |
| | Ultrasonic treatment | 5.6 | 6.0 | 5.8 | 6.2 | 6.4 | 10.0 | 9.5 |
| | Difference (no ultrasonic treatment-ultrasonic treatment) | 0.2 | 0.0 | 0.5 | 3.6 | 8.0 | 9.8 | 6.4 |

Discussion

It can be seen in Table 4 that the mean particle size of Compound (II) does not differ greatly before and after sonication in Examples 7, 8 and 9. The difference was only 0.2 μm in Example 7, in which the silicone oil was contained at 0.025 weight parts relative to 100 weight parts of Compound (II), only 0.0 μm in Example 8, in which the silicone oil content was 0.05 weight parts, and only 0.5 μm in Example 9, in which the silicone oil content was 0.1 weight parts. The results thus demonstrated that Compound (II) was desirably dispersed without agglomerating.

On the other hand, the mean particle size of Compound (II) was relatively large, i.e., 9.8 μm and 14.4 μm, before sonication, and reduced to 6.2 μm and 6.4 μm after sonication respectively in Comparative Example 7, which contained 0.5 weight parts of silicone oil relative to 100 weight parts of Compound (II), and in Comparative Example 8, which contained 1 weight part of silicone oil. Because sonication reduced the mean particle size, it was found that agglomeration occurred in the Compound (II) present in the suspension of Comparative Examples 7 and 8, and that the Compound (II) could not be dispersed without a special treatment such as sonication. In Comparative Examples 9 and 10, which contained silicone oil at 2.5 and 5 weight parts, the Compound (II) had very large mean particle sizes of 19.8 μm and 15.9 μm before sonication. Sonication reduced the mean particle size to 10.0 μm and 9.5 μm. However, the agglomeration was so severe that sonication was not sufficient to restore the original particle size of about 5.3 μm. These results thus demonstrated that agglomeration becomes more severe with increases in the silicone amount.

The freeze-dried cakes containing Compound (II) showed the same results as those observed in Examples 3 to 6 using aripiprazole.

The invention claimed is:
1. A method for reducing active ingredient particles from agglomerating in a suspension;

the suspension containing an active ingredient and at least one of silicone oil and silicone oil derivative in a dispersion medium;

the active ingredient being at least one member selected from the group consisting of aripiprazole and a compound of formula (II):

(II)

the active ingredient being in a form of particles having a mean primary particle size of 0.1 μm or larger and smaller than 200 μm;

the method comprising mixing the active ingredient with the at least one of silicone oil and silicone oil derivative in a dispersion medium, in such a manner that the at least one of silicone oil and silicone oil derivative is contained in an amount of 0.001 to 0.2 weight parts relative to 100 weight parts of the active ingredient contained in the suspension.

2. The method according to claim 1, wherein the active ingredient is aripiprazole.

3. The method according to claim 1, wherein the active ingredient is the compound of formula (II):

(II)

4. A suspension comprising an active ingredient and at least one of silicone oil and silicone oil derivative in a dispersion medium;

the active ingredient being at least one member selected from the group consisting of aripiprazole and a compound of formula (II):

(II)

the active ingredient being in a form of particles and having a mean primary particle size of 0.1 μm or larger and smaller than 200 μm; and the at least one of silicone oil and silicone oil derivative being contained in an amount of 0.001 to 0.2 weight parts relative to 100 weight parts of the active ingredient contained in the suspension.

5. The suspension according to claim 4, wherein the active ingredient is aripiprazole.

6. The suspension according to claim 4, wherein the active ingredient is the compound of formula (II):

(II)

7. A cake composition comprising an active ingredient and at least one of silicone oil and silicone oil derivative;

the active ingredient being at least one member selected from the group consisting of aripiprazole and a compound of formula (II):

(II)

the active ingredient being in a form of particles and having a mean particle size of 0.1 μm or larger and smaller than 200 μm; and the at least one of silicone oil and silicone oil derivative being contained in an amount of 0.001 to 0.2 weight parts relative to 100 weight parts of the active ingredient contained in the cake composition.

8. The cake composition according to claim 7, wherein the active ingredient is aripiprazole.

9. The cake composition according to claim 7, wherein the active ingredient is the compound of formula (II):

(II)

* * * * *